(12) United States Patent
Keller

(10) Patent No.: US 7,601,148 B2
(45) Date of Patent: Oct. 13, 2009

(54) INFUSION PUMP

(76) Inventor: Hermann L. Keller, 45, CH-4502 Basel (CH)

( * ) Notice: Subject to any disclaimer, the term of this patent is extended or adjusted under 35 U.S.C. 154(b) by 80 days.

(21) Appl. No.: 10/495,069

(22) PCT Filed: Nov. 6, 2002

(86) PCT No.: PCT/CH02/00596

§ 371 (c)(1),
(2), (4) Date: Nov. 10, 2004

(87) PCT Pub. No.: WO03/039631

PCT Pub. Date: May 15, 2003

(65) Prior Publication Data

US 2005/0063838 A1    Mar. 24, 2005

(30) Foreign Application Priority Data

Nov. 6, 2001   (CH) .................................... 2034/01

(51) Int. Cl.
*A61K 9/22* (2006.01)
(52) U.S. Cl. .................................... 604/890.1
(58) Field of Classification Search ............. 604/890.1, 604/981.1, 131, 151, 152, 153, 132, 246, 604/288.01–288.04; 417/413.2, 313
See application file for complete search history.

(56) References Cited

U.S. PATENT DOCUMENTS

| | | | | |
|---|---|---|---|---|
| 2,891,700 A | * | 6/1959 | Maynard | 222/92 |
| 4,191,181 A | * | 3/1980 | Franetzki et al. | 604/151 |
| 4,519,751 A | * | 5/1985 | Beckman et al. | 417/322 |
| 4,596,575 A | | 6/1986 | Rosenberg et al. | |
| 4,822,250 A | | 4/1989 | Tsubouchi et al. | |
| 4,944,659 A | * | 7/1990 | Labbe et al. | 417/413.2 |
| 5,113,859 A | | 5/1992 | Funke | |
| 5,176,641 A | * | 1/1993 | Idriss | 604/133 |
| 5,224,843 A | | 7/1993 | van Lintel | |
| 5,354,282 A | * | 10/1994 | Bierman | 604/180 |
| 5,569,187 A | | 10/1996 | Kaiser | |
| 5,928,195 A | * | 7/1999 | Malamud et al. | 604/141 |
| 5,941,421 A | * | 8/1999 | Overman et al. | 222/105 |
| 6,074,178 A | * | 6/2000 | Bishop et al. | 417/322 |
| 6,464,671 B1 | | 10/2002 | Elver et al. | |

FOREIGN PATENT DOCUMENTS

| | | |
|---|---|---|
| DE | 2421433 A1 | 11/1975 |
| RU | 2030634 C1 | 3/1995 |

OTHER PUBLICATIONS

International Search Report for PCT/CH02/00596 dated Jan. 7, 2003.

* cited by examiner

*Primary Examiner*—Nicholas D Lucchesi
*Assistant Examiner*—Christopher D Koharski
(74) *Attorney, Agent, or Firm*—Bachman & LaPointe, P.C.

(57) ABSTRACT

Known variable flow pumps (VF pumps) are characterized by significant inaccuracies in the delivery quantities. In addition, they cause cosmetic problems in the carrier after implantation as a result of their external configuration. The invention provides an implantable VF pump, which resolves the disadvantages. To achieve this, the battery-driven delivery device is configured according to piezoelectric principles and the external surface of the upper pump housing shell is provided with expansion joints.

3 Claims, 4 Drawing Sheets

Figure 5:
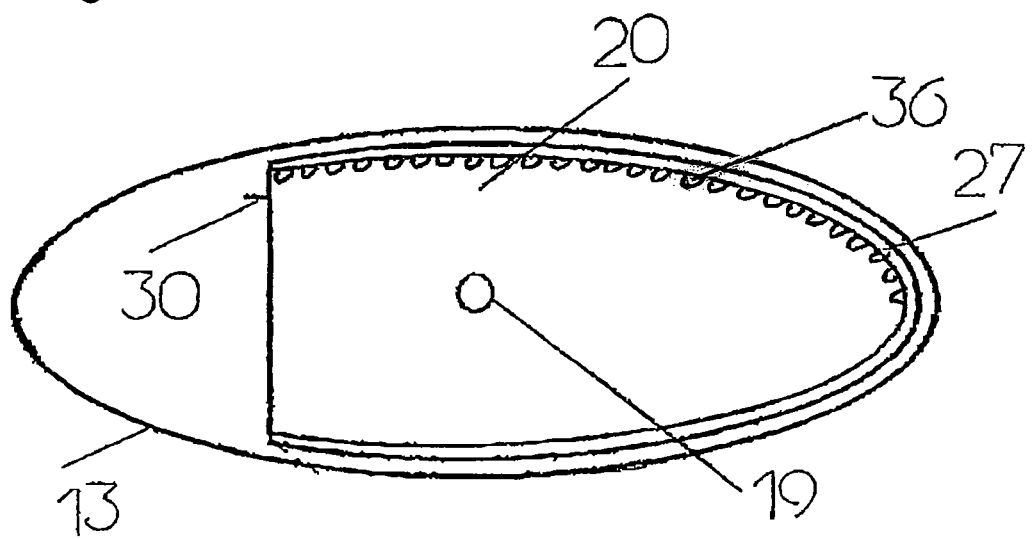

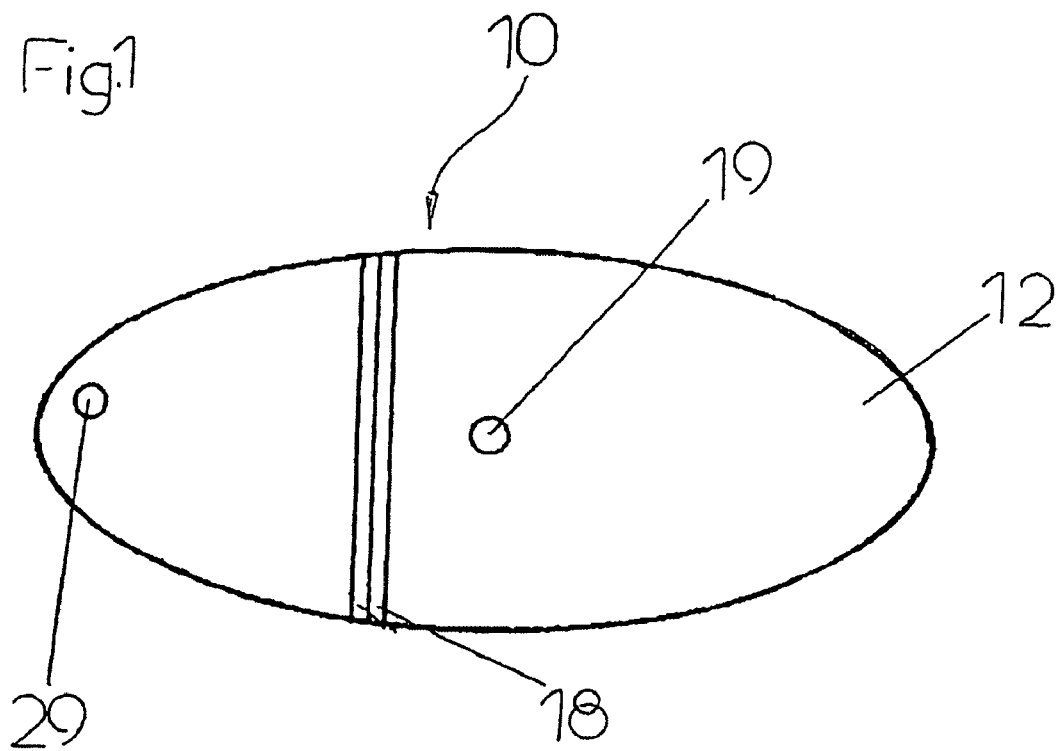
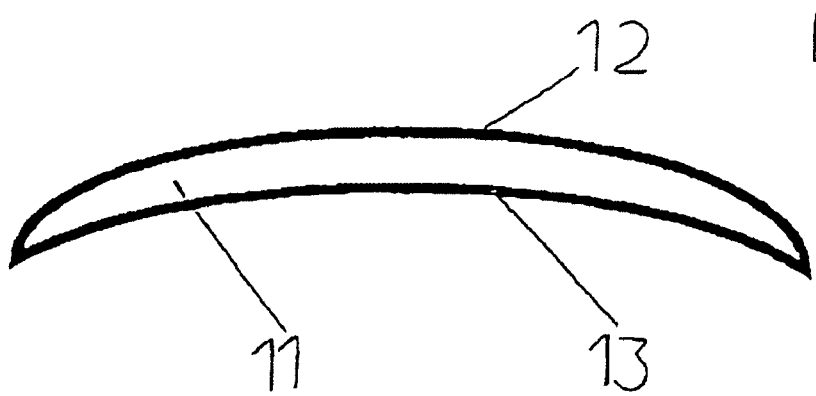

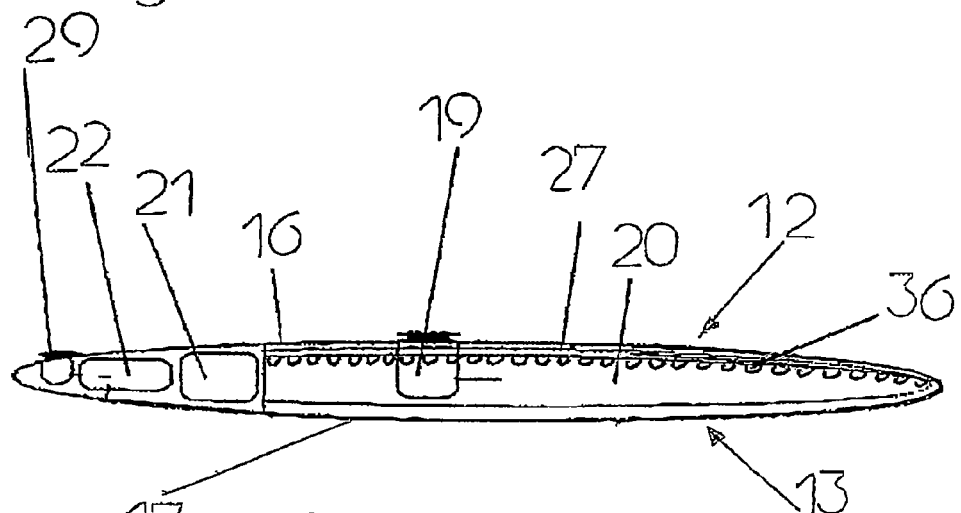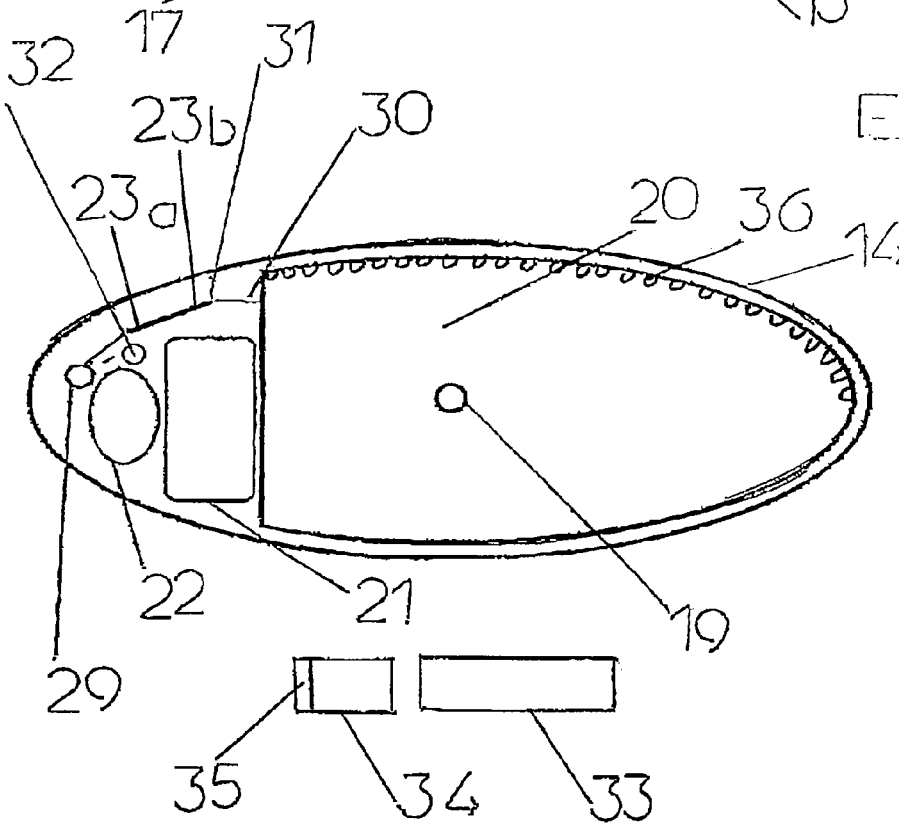

Fig 7
24c  24b  24a
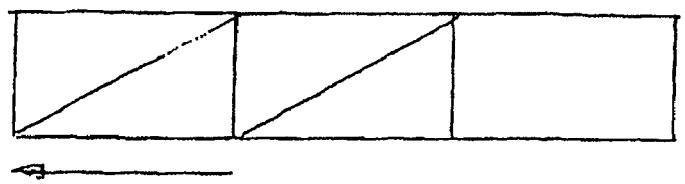 6
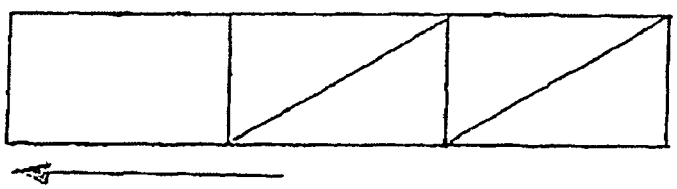 5
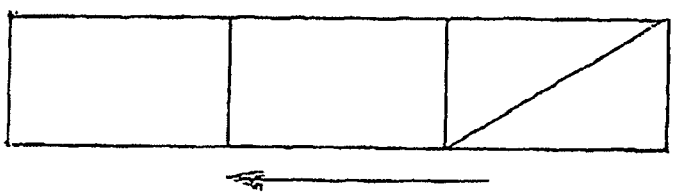 4
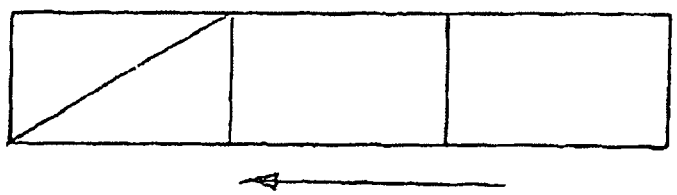 3
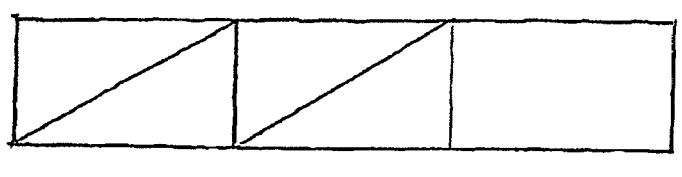 2
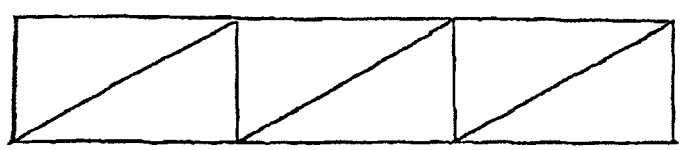 1

INFUSION PUMP

The invention relates to an infusion pump in accordance with the preamble of patent claim 1.

Various methods and devices are known for carrying out infusion—by which is meant the introduction of fluids for example into a human or animal body. A known method is that of intravenous infusion, in which a fluid is delivered by gravity from a container which releases defined quantities of fluid per unit of time, these quantities of fluid being delivered to a vein via a delivery line, usually a tube. This method and the device used to perform it are known by the abbreviated term "drip infusion", which is technically straightforward and reliable, but is only suitable for use in patients whose freedom of movement is restricted.

To overcome these limitations, so-called metering pumps (referred to hereinbelow simply as pumps) have been developed and used which the recipient of the delivered medium constantly carries on his or her person in order to maintain his or her freedom of movement. Pumps generally comprise a housing which accommodates a refillable container for medium, i.e. fluid or medication, and a device for delivering the medium to the attachment point of a delivery line leading from said device. The delivery line, also called a catheter, can empty for example into the intrathecal space or into the blood stream, depending on the medical indication presented by the recipient.

Depending on the pump design, a differentiation is made between variable flow pumps (VF pumps) and constant flow pumps (CF pumps). VF pumps are pumps whose delivery rate per unit of time is adjustable, whereas the delivery rate per unit of time in CF pumps is invariable, i.e. constant. As a mechanical means for delivering the medium from the storage container to the catheter attachment, the VF pump has a battery-driven roller pump whose operating parameters, such as speed of rotation, delivery rate, etc., can be adjusted electronically via a chip. The operating parameters are changed by means of data being transmitted to the chip from a data-processing device, e.g. a computer, via a cable and a read head. The filling level of the storage container, and thus the consumption over a specified time period, is not measured in VF pumps, but calculated. This means that it is not the filling level that indicates the need for refilling, and instead, after a predetermined period of time which has been input on the chip, refilling takes place independently of the remaining quantity of media in the storage container. If, as regards VF pumps, one considers the quite substantial operating inaccuracies of the roller pumps, i.e. deviations of plus/minus 10% to 15% in delivery rate from a set delivery rate value, it becomes clear that relatively large residual quantities of media, i.e. medicaments, have to be provided before a refilling signal is triggered. Residual quantities have to be drawn off from the storage container prior to refilling and cannot be used again. In the case of expensive medicaments, this circumstance greatly increases the cost of operating a pump. The adjustable VF pump may have the advantage of being able to be programmed whenever required, but this advantage has to be seen against the disadvantages that the required programming can be undertaken only by specially trained medical personnel, that, because of the transmission by way of a cable between computer and read head, a patient has to get to the data-processing unit, or vice versa, and that relatively large residual quantities of medicaments have to be factored in as a result of operating inaccuracies.

A CF pump is of simpler design compared to a VF pump. The medium is delivered from the storage container to the catheter attachment by means of a pressurized gas cushion, a reducer device being provided between storage container and catheter attachment in order to define an invariable throughput rate per unit of time. CF pumps are tailored to the particular patient; only the composition of the delivery medium can be varied, not however, as in the VF pump, delivery rate and composition. The time at which refilling takes place is determined during a previous filling procedure on the basis of the known throughput rates. The delivery accuracy, i.e. the accuracy of a throughput rate per unit of time, is greater than in VF pumps, so that residual quantities do not pose the same problem as in VF pumps. The advantages of the simple design and greater delivery accuracy compared to VF pumps and the possibility of refilling being carried out by non-specialized medical personnel have to be seen against the disadvantage of limited possibilities of adjustment.

The majority of pumps of the described type are implanted in the users, i.e. the patients. They are implanted in the abdominal region between muscles and skin, i.e. in the subcutaneous fatty tissue. The housings of the pumps are designed as boxes, normally having a diameter of ca. 8 cm and a height of ca. 2 cm to 2.5 cm, the weight of the pumps being of the order of ca. 200 g. The design and weight of the pumps lead, after implantation, to a cosmetic problem for the patient since the implantation area undergoes considerable deformation on account of the box shape and the weight.

Starting out from this prior art, the inventors set themselves the object of creating a pump which has the advantages of the known pumps, but not their disadvantages, and this object is achieved with a pump having the characterizing features of patent claim 1.

Advantageous embodiments of a pump as claimed in patent claim 1 are characterized by the features set out in the patent claims following patent claim 1.

Figure 6:
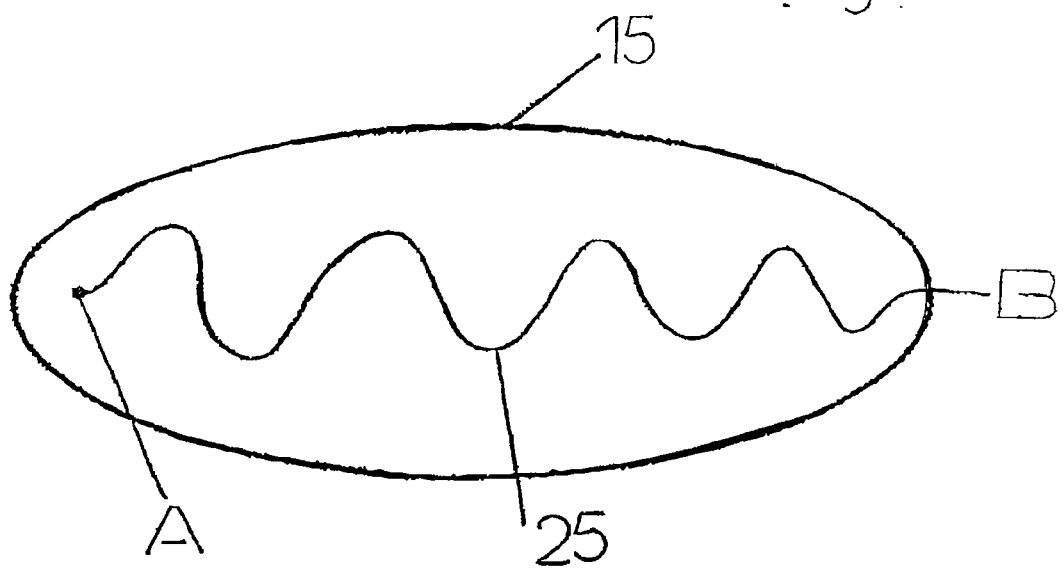

Further advantages, features and details of the invention will become clear from the following description of a preferred illustrative embodiment and from the drawing, in which:

FIG. 1 shows a plan view of the upper shell of a pump,

FIG. 2 shows a side view of the pump according to FIG. 1, adapted to the shape of the implantation site in a patient's body, FIG. 3 shows a central vertical section through the pump according to FIG. 1 in a side view, FIG. 4 shows a horizontal section through the pump according to FIG. 1 in a plan view, the reservoir and reservoir liner being supplemented by other component parts of the pump, FIG. 5 shows a horizontal section through the pump according to FIG. 1 in a plan view, with only the reservoir and reservoir liner showing in the section, FIG. 6 shows a plan view of the lower shell of a pump according to FIG. 1, FIG. 7 shows a diagrammatic representation of the circuits 1 to of a piezo pump.

According to FIG. 1, the pump 10 according to the invention comprises a housing 11 in which the component parts of the pump 10 are accommodated. The housing 11 is made up of two identical half-shells, namely an upper shell 12 and a lower shell 13, which engage with one another, i.e. are connected to one another, via their free peripheral edges (edge of the upper shell 14, edge of the lower shell 15). The connection is fluid-tight, so that the component parts of the pump 10 are sealed off and protected against ingress of fluid. The edges 14, 15 of the upper shell 12 and lower shell 13 describe an ellipse, while the outer surfaces 16, 17 of the shells 12, 13, starting from their center points, extend radially out to the edges 14, 15 in the longitudinal direction and transverse direction of the shells 12, 13. This results in a relatively thin housing 11 which decreases in size all around from its center point outward, i.e. has flowing contours which make an important contribution to eliminating the cosmetic problems known from the prior art and caused by the cylinder shape of the known pumps. To completely eliminate the cosmetic problems, the housing 11 of the pump 10 is of an arc-shaped design, the deformation during implantation taking place according to the shape or contour of the implantation site. Pumps are implanted in humans in the abdominal region, between muscle and skin, i.e. in the subcutaneous fatty tissue, which accommodates the housing according to the invention without outward bulging, i.e. away from the implantation site. The upper shell 12 has expansion joints 18 which promote the arc-shaped deformation, i.e. the adaptation of the housing 11 to the shape of an implantation site. In this deformation, the upper shell 12 experiences an expansion, whereas the lower shell 13 is compressed. Normally, the compressions can take place without compensating means; however, if it is necessary or expedient to compensate for compression or make it easier, compensation joints can also be arranged on the lower shell. Joints 18 preferably extend transversely with respect to the longitudinal axis, from edge to edge of the shells, and they are dimensioned such that they can be expanded or contracted. Housings 11 are preferably made of plastics, preferably plastics curing by UV (ultraviolet light). UV-curing plastics for housings 11 are advantageous because the housings 11 can be readily plasticized before or during the implantation procedure, can be adapted to the shape of the implantation site and then hardened again by UV.

The component parts accommodated in the housing 11 of the pump 10 comprise a reservoir 20 with piercing mandrel 19 for reservoir-filling, a battery 21, an electronic control unit 22, a delivery device 23 operating according to the piezoelectric principle (hereinafter called piezo pump 23), delivery devices, e.g. tubes, for delivering the fluid contained in the reservoir from reservoir 20 to piezo pump 23 and from there to a side port 29, and electrical leads which connect the battery 21 to the control unit 22 and the latter to the piezo pump 23.

In its physical configuration, the reservoir 20 corresponds to the internal cavity of the housing 11, but is shortened along its longitudinal axis by a peripheral edge 26 extending at right angles to the longitudinal axis, so that the other component parts of the pump too can be accommodated in the interior of the housing 11. The reservoir 20, i.e. its walls are made of a flexible plastic film which is resistant to acid and alkali and which on one side has naps 36, hereinafter called nap film. After production of the reservoir 20, the surface of the film provided with naps 36 forms the inner surface of the reservoir walls. The naps 36 ensure that, when the reservoir 20 is empty, the inner surfaces of the walls do not stick together. The reservoir 20 is surrounded by a pressure body 27. The pressure body 27 is made of a compressible and expandable synthetic foam. Its outer shape corresponds to the shape of the hollow cavity of the housing 11, while its inner shape is dimensioned such that the reservoir 20 is accommodated therein with upper and lower reservoir walls bearing on one another. When the reservoir is filled, it expands, and the upper and lower reservoir walls compress the foam against the inner surface of the housing 11. By means of this compression, the foam of the pressure body 27 exerts on the reservoir 20 a counter-force, which decreases as the reservoir 20 empties. The fact that pressure is applied all round to the reservoir 20 ensures that it empties completely and guarantees that the pump 10 delivers fluid in every position.

The reservoir 20 is filled via a valve 19 (also called piercing mandrel 19) which, starting from the upper shell 12, engages through the shell 12, the pressure body 27 and a reservoir wall and opens into the reservoir 20. The piercing mandrel 19 is in principle a valve which can be opened in one direction for filling and is kept closed after filling. The reservoir 20 has an outlet 30 which is connected to the input side 31 of the piezo pump 23 via a delivery line, for example a tube. In this way, the input side 31 of the piezo pump 23 is afforded a constant delivery of fluid.

The piezo pump 23 is a tube made of piezoelectric crystals and comprises at least two tube portions 23a and 23b, and it is possible to apply a current or voltage individually to each tube portion 23a, 23b via lines (not shown in detail). It is known that piezoelectric crystals react to an applied electrical voltage or an applied current by changing their lattice structure. For example, if a voltage is applied to the crystal, the lattice structure expands, and, if voltage is withdrawn from the crystal, the lattice structure contracts. This effect is used by the piezo pump 23, with a current or a voltage being able to be applied to or removed from each of the tube portions 23a, 23b. If a current or a voltage is applied to the tube portions 23a, 23b, the latter widen together with their bores (bore opens up), and if the current or the voltage is removed, they contract together with their bore (bore closes). To generate a pump operation, the tube portions 23a, 23b are electrically oppositely switched. If a current is applied to the tube portion 23a, the described widening takes place, i.e. the bore of the tube portion 23a is open and can receive a fluid. While fluid is received, no current is applied to the tube portion 23b, the tube portion 23b is closed. Once the intake of fluid (filling procedure) in tube portion 23a is completed, the current applied to tube portion 23a is removed and a current is applied to tube portion 23b, so that tube portion 23a closes and tube portion 23b opens, and the fluid is output from the bore of tube portion 23a and flows through the bore of tube portion 23b. Once this is completed, current is removed from the tube portion 23b and current is applied to tube portion 23a, whereupon the pumping procedure repeats itself, with the tube portion 23b, as the last portion of successively arranged portions in the delivery direction, acting in the closed state as a nonreturn valve. The switching-off of current to tube portion 23a takes place just before switching-on of current to tube portion 23b, so that, through the contraction of the bore of the tube portion 23a, pressure is applied to the fluid in tube portion 23b which is still closed, so that the fluid flows out at higher pressure from the tube portion 23b than when it flowed into the tube portion 23a. The invention is not limited to a piezo pump 23 with two tube portions 23a, 23b. Piezo pumps according to the invention can be made up of more than two tube portions. This is expedient when greater pressures of the fluid are needed (the pressure increases in the delivery direction with each tube portion). Another factor is that greater and more accurate quantities of fluid can be dispensed with an increasing number of tube portions.

The function of a multi-stage pump, in the case shown a three-stage piezo pump 23, is described below with reference to FIG. 7. The piezo pump 23 according to FIG. 7 comprises three tube portions 24a, 24b, 24c (called portions 24a, 24b, 24c below) which can each be activated piezoelectrically, for example by application of a current, and deactivated. The figure shows 6 circuits (circuits 1 through 6). Each portion 24a, 24b, 24c is shown as a rectangle, and a rectangle without a diagonal line signifies that the portion is open, while a rectangle with a diagonal line means that the portion is closed. The arrows shown indicate the direction of flow.

In circuit 1, no current or voltage is applied to the pump 23 or to any of its portions 24a, 24b or 24c, so that the pump is without current and therefore closed, with all portions being closed. This is a safety feature designed according to the invention which ensures that, if the battery 21 fails, the closed portions prevent introduction of body fluid into the reservoir 20.

In circuit 2, a current is applied to portion 24a, so that portion 24a opens and is filled from the reservoir 20. The portions 24b and 24c are closed.

In circuit 3, the portions 24a and 24b are supplied with current, so that the portion 24b opens and, together with the open portion 24a, forms an increased filling space which, as a supplement to the filling quantity in portion 24a, is filled from the reservoir 20 with a quantity corresponding to the portion 24b. The filling operations in circuits 2 and 3 are performed predominantly by suction, the suction procedure being triggered by opening of the portions 24a, 24b. During the two-stage suction procedure, the piezo pump 23 and reservoir 20 are protected against pressurized body fluid by the last closed portion 24c in the flow direction. Pressure is built up when, during the closing of 24a (circuit 4), the filled quantity is forced from 24a and 24b toward the closed portion 24c, said portion 24c being opened with a brief delay after portion 24a.

In circuit 4, the portion 24a is closed, and portions 24b and 24c are open. The filled quantity originally received in portion 24a and portion 24b moves, under higher pressure, into the portions 24b and 24c, so that a first subsidiary quantity of the filling is delivered.

In circuit 5, the portion 24b closes, and the closure procedure presses the second subsidiary quantity out of the piezo pump 23.

In circuit 6, portion 24c is closed and portion 24a is opened again, the pump is returned to circuit 2 for a next pumping procedure consisting of filling (circuits 2 and 3), pressure build-up (circuit 3, closure 24a and circuit 4, briefly delayed opening), delivery (circuits 4 and 5), filling (circuit 6, identical to circuit 2).

In contrast to the prior art, which assigns the pump function to mechanical devices (roller pumps), the invention takes a different approach by giving the pump function to a piezo-electrically activatable and deactivatable tube made up of at least two tube portions. Tubes with this kind of operation are wear-free and can be operated with less energy than pumps with mechanical delivery devices, and pumps according to the invention are characterized by the fact that they are much lighter than known pumps. A particular advantage is that the precision of successive delivery rates is in excess of 99%. This high degree of precision of delivery means that, in the case of administering medicaments, smaller quantities at higher concentration can be administered per delivery procedure than is possible with pumps according to the prior art.

One tube connects the downstream end of the pump 23 to an attachment 29, called side port 29 below. The side port 29 engages through the lower shell 13 and the catheter 25 provided outside the housing 11 is attached to it with its upstream end A, while the downstream end B, depending on the indication, empties for example into the intrathecal space or the blood stream of a recipient. On its outer surface 17, the lower shell 13 has a recess of wave-shaped form in which the catheter 25 is placed. In this way, the catheter 25 can be connected to the pump 23 in a manner free from kinking and stress. Moreover, a length of tube is also made available which, in order to avoid catheter tears, compensates for longitudinal expansions of the catheter 25 caused by movements of the body. The side port 29 is designed first of all as a catheter attachment on the lower shell 13 and as a valve opening into the catheter attachment, which valve engages through the upper shell 12 and into which additional quantities of fluid, for example medical composition, can be added by injection (syringe with needle) to the fluid stream from the outside as the pump 23 is running. With the pump 23 switched off, the side port 29 can be used for flushing the catheter and for leaktightness tests.

For the piercing mandrel 19 and the similarly acting side port 29, valves are preferred which are made of medically acceptable titanium with a silicone filler performing a valve function. For the filling procedure, the silicone filler is for example pierced with a hollow needle, and the hollow needle is withdrawn after the filling procedure, and the pierced opening through the silicone filler closes. Valves of this kind are of simple design and have no movable parts, and they are characterized by a high level of operating reliability.

The implantable battery 21 is electrically connected to the piezo pump 23 via an electronic control unit 22. The purpose of the control unit is to supply current from the battery 21 to the piezo pump 23 in impulses. The time sequence between the impulses which the switching on and off of the current (hereinbelow called the pump impulse) and a following impulse is determined by a clock quartz which triggers the impulses according to defined summated oscillations via the control unit. These oscillation numbers are stored on a data storage device (microchip) so that they can be called up and changed. The frequency per unit of time with which the pump impulses are triggered is referred to below as the clock frequency. The programming of the control unit 22, i.e. of the chip, includes the maximum quantity a piezo pump 23 can deliver during a pump impulse, and this is input to the chip as a fixed and unalterable parameter. This means that each piezo pump 23 is individually calibrated during its manufacture, as a result of which each piezo pump 23 becomes an identifiable, patient-specific entity with its own technical data. The maximum delivery rate as constant parameter set in relation to the clock frequency enables the chip to calculate the delivery rate, residual quantity, etc. Reference number 32 indicates a magnet switch which can be activated and deactivated only by means of a code and, in one of the two states, permits access to the chip of the control unit 22 for the purpose of altering data. After implantation of the pump 10, the chip of the electronic control unit 22 can also provide information on the medicament, the original filling quantity, the quantity of an individual administration (dose) per pump impulse, the clock frequency, the total quantity of the administered medicament, the residual quantity in the reservoir 20, the running time of the pump 10, the status of the battery, identification (registration) of the pump 10, and, if programmed by the physician, the number of boluses (medicament portions) which a patient has additionally self-administered by means of the pump 10 in addition to the portions delivered as programmed by the pump 10, together, for example, with the date and time of the additional administrations. The above items of information are partially calculated or recorded on the chip. For example, the residual quantity in the reservoir 10 is calculated, its status for emergency signals for reservoir refilling, warning of increased fluid consumption, total quantity delivered, etc.

The electronic control unit 22 of the pump 10 interacts with a data-processing device 33 (called data processor 33 below) which communicates with the electronic control unit 22, i.e. its data-carrying memory or chip, via a free read head 34. The data processor 33, for example a conventional personal computer, is available to the physician, while the patient has the read head 34, which is not implanted, at his or her disposal. On the data processor 33, all therapy-related values and all values specific to the pump operation are defined and stored via a program and transferred via the read head 34 to the chip of the control unit. The transfer is effected by the patient holding the read head 34 on the implanted pump 10, i.e. he brings the chip and read head 34 into communicative engagement with one another. In the reverse direction, the read head can pick up data from the chip and return it to the data processor 33 for editing. After the initial programming of the chip and implantation of the pump 10, the control unit 22 and data processor 33 remain linked up for call-up via the read head 34, and the physician can for example call up data from the chip via the read head 34, compare it, change it for therapeutic purposes and return it to the chip. According to the invention, the data transfer from data processor 33 to the read head 34 is preferably done via telephone lines or similar telephony devices using so-called tone dialling, which assigns data and tones to different tone sets and transmits them. This kind of data transmission is possible over great distances, so that the physician can carry out therapeutic measures even when located a considerable distance from the patient.

If bolus administration is programmed according to the medical prescription, the read head 34 can then be combined with a signal emitter 35 which triggers only the bolus administration.

The pump 10 according to the invention is characterized, as has been described, by two operating modes. The first operating mode (mode 1) is the delivery of defined quantities in the context of a predetermined clock frequency, the second operating mode (mode 2) includes the first, supplemented if appropriate by administration of additional quantities (bolus). In the medical application of the pump 10 according to the invention, mode 1 is based, in terms of quantities delivered, incidence of delivery, composition of the medicaments etc., on the experience of the physician, who endeavors to come as close as possible to his therapeutic objective. If insufficiencies, for example the blood sugar level of a diabetic, do not fluctuate, then it is enough to operate the pump 10 without bolus administration according to the medical prescription (programmed insulin administration). If insufficiencies fluctuate, and if they subjectively affect the patient, then mode 2 is preferred, because with mode 2 the prescription by the physician in accordance with mode 1 can be supplemented or modified by the patient in order to eliminate disturbances. If one assumes that mode 1 follows medical knowledge and generally recognized empirical rules, in other words an objective therapeutic approach, then mode 2 involves an added subjective element which does not permit any conclusions concerning the level of the fluctuations. In order to counteract this, a sensor (not shown) measuring fluctuations can be provided for bolus administration, which sensor measures deviations from set values according to mode 1 and, if the pump 10 exceeds or falls below these, sends a command to the pump 10, i.e. to the chip of the control unit 22, to deliver additional quantities/smaller quantities in order to compensate for the fluctuations. Sensors can, for example, be implanted in the blood stream of a diabetic or, where indicated, can be worn on the body.

The invention claimed is:

1. An infusion pump to be implanted in the abdominal region of a patient comprising a housing, a reservoir which is received in the housing and can be filled with a fluid and has a piercing mandrel and outlet, a catheter, means for delivering fluid from the reservoir to the catheter, the means for delivery disposed outside the reservoir and whose delivery rate can be adjusted via an electronic control unit, wherein the means for delivery comprises a piezoelectric pump, the housing has a longitudinal axis and comprises an arc-shaped upper half-shell and an arc-shaped lower half-shell, each half- shell has a peripheral edge in the form of an ellipse and the peripheral edges are connected together in a fluid tight manner and form an arc-shaped housing, the upper half-shell is provided with at least one expansion joint which extends horizontally with respect to the longitudinal axis of the housing to promote an arc-shaped deformation of the housing when implanted in the abdominal region of the patient, wherein the upper shell experiences expansion and the lower shell is compressed.

2. The infusion pump as claimed in claim 1, wherein the reservoir (20) is made of a flexible film.

3. The infusion pump as claimed in claim 2, wherein the reservoir (20) is received in a pressure body (27) made of a compressible synthetic foam.

* * * * *

UNITED STATES PATENT AND TRADEMARK OFFICE
CERTIFICATE OF CORRECTION

PATENT NO.       : 7,601,148 B2  
APPLICATION NO.  : 10/495069  
DATED            : October 13, 2009  
INVENTOR(S)      : Hermann L. Keller It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 267 days.

Signed and Sealed this

Fifth Day of October, 2010

David J. Kappos  
*Director of the United States Patent and Trademark Office*